US008742171B2

(12) United States Patent
Fachinetti et al.

(10) Patent No.: US 8,742,171 B2
(45) Date of Patent: Jun. 3, 2014

(54) PROCESS FOR PREPARING FORMIC ACID

(75) Inventors: Giuseppe Fachinetti, Pisa (IT); Debora Preti, Nodica-Vecchiano (IT)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/492,332

(22) Filed: Jun. 8, 2012

(65) Prior Publication Data

US 2013/0006015 A1 Jan. 3, 2013

Related U.S. Application Data

(60) Provisional application No. 61/494,896, filed on Jun. 9, 2011.

(51) Int. Cl.
*C07C 53/02* (2006.01)

(52) U.S. Cl.
USPC .......................................................... 562/609

(58) Field of Classification Search
CPC ..................................................... C07C 51/13
See application file for complete search history.

(56) References Cited

U.S. PATENT DOCUMENTS

| 5,506,273 | A | * | 4/1996 | Haruta et al. ................. 518/713 |
|---|---|---|---|---|
| 8,426,641 | B2 | | 4/2013 | Schaub et al. |
| 2008/0097126 | A1 | | 4/2008 | Karl et al. |
| 2010/0331573 | A1 | | 12/2010 | Schaub et al. |
| 2011/0319657 | A1 | | 12/2011 | Schneider et al. |
| 2011/0319658 | A1 | | 12/2011 | Schaub et al. |
| 2012/0022290 | A1 | | 1/2012 | Schaub et al. |
| 2012/0071690 | A1 | | 3/2012 | Pazicky et al. |
| 2012/0157711 | A1 | | 6/2012 | Schaub et al. |
| 2013/0012739 | A1 | | 1/2013 | Schaub et al. |
| 2013/0090496 | A1 | | 4/2013 | Schaub et al. |
| 2013/0102807 | A1 | | 4/2013 | Schaub et al. |
| 2013/0123526 | A1 | | 5/2013 | Schaub et al. |
| 2013/0190532 | A1 | | 7/2013 | Schneider et al. |

FOREIGN PATENT DOCUMENTS

| CA | 2821642 | | 6/2012 |
|---|---|---|---|
| CN | 1593753 | A | 3/2005 |
| EP | 0 095 321 | A2 | 11/1983 |
| EP | 0151510 | A1 | 8/1985 |
| EP | 0181078 | A1 | 5/1986 |
| EP | 0 357 243 | A2 | 3/1990 |
| EP | 0597151 | A1 | 5/1994 |
| JP | 2009-190981 | | 8/2009 |
| SG | 186045 | | 1/2013 |
| SG | 186264 | | 1/2013 |
| SG | 186768 | | 2/2013 |
| WO | WO-2006/021411 | A1 | 3/2006 |
| WO | WO-2010/149507 | A2 | 12/2010 |
| WO | WO-2012/000799 | | 1/2012 |
| WO | WO-2012/000823 | | 1/2012 |
| WO | WO-2012/000964 | | 1/2012 |
| WO | WO-2012/034991 | | 3/2012 |
| WO | WO-2012/084691 | | 6/2012 |

OTHER PUBLICATIONS

International Search Report for PCT/EP2012/060845, mailing date Sep. 20, 2012.
Jessop, Philip G., "Homogenous Hydrogenation of Carbon Dioxide", The Handbook of Homogenous Hydrogenation, vol. 1, (2007), pp. 489-511.
Fellay, Celine, et al., "Selective Formic Acid Decomposition for High-Pressure Hydrogen Generation: A Mechanistic Study", Chem. Eur. J., vol. 15, (2009), pp. 3752-3760.
Baiker, Alfons, "Utilization of Carbon Dioxide in Heterogeneous Catalytic Synthesis", Applied Organometallic Chemistry, vol. 14, (2000), pp. 751-762.
Zhang, Zhaofu, et al., "Hydrogenation of $CO_2$ to Formic Acid Promoted by a Diamine-Functionalized Ionic Liquid", ChemSusChem, vol. 2, (2009), pp. 234-238.
Henkel, Klaus-Dieter, "Reactor Types and Their Industrial Applications", Ullmann's Encyclopedia of Industrial Chemistry, (2005), pp. 1-33.
International Search Report SIPO (Chinese Patent Office) for PCT/IB2012/052891, mailing date Sep. 27, 2012.
Ullmann's Encyclopedia of Industrial Chemistry, "Methanol", Mathematics in Chemical Engineering to Microencapsulation, 6th ed., vol. 21, (2003), pp. 611-635.
U.S. Appl. No. 61/578,900.
U.S. Appl. No. 61/512,023.
U.S. Appl. No. 61/532,579.
U.S. Appl. No. 61/557,947.
U.S. Appl. No. 61/578,901.

\* cited by examiner

*Primary Examiner* — Paul A Zucker
(74) *Attorney, Agent, or Firm* — Drinker Biddle & Reath LLP (57) ABSTRACT

A process for preparing formic acid by hydrogenation of carbon dioxide in the presence of a tertiary amine (I) and a catalyst at a pressure of from 0.2 to 30 MPa abs and a temperature of from 20 to 200° C., wherein the catalyst is a heterogeneous catalyst comprising gold.

12 Claims, 8 Drawing Sheets

PROCESS FOR PREPARING FORMIC ACID

CROSS-REFERENCE TO RELATED APPLICATIONS

This application claims benefit under 35 U.S.C. §119(e) of U.S. Provisional Patent App. Ser. No. 61/494,896, filed Jun. 9, 2011, which is incorporated herein by reference in its entirety.

This patent application claims the benefit of pending U.S. provisional patent application Ser. No. 61/494,896 filed Jun. 9, 2011 incorporated in its entirety herein by reference.

The present invention relates to a process for preparing formic acid by hydrogenation of carbon dioxide in the presence of a tertiary amine (I) and a catalyst at a pressure of from 0.2 to 30 MPa abs and a temperature of from 20 to 200° C.

Formic acid is an important and versatile product. It is used, for example, for acidification in the production of animal feeds, as preservative, as disinfectant, as auxiliary in the textile and leather industry, as a mixture with its salts for deicing aircraft and runways and also as synthetic building block in the chemical industry.

The commonest process at present for the preparation of formic acid seems to be the hydrolysis of methyl formate. The aqueous formic acid obtained by hydrolysis is subsequently concentrated, for example by use of an extracting agent such as, for example, a dialkylformamide.

In addition, it is known that formic acid can also be obtained by thermal cleavage of compounds of formic acid and a tertiary nitrogen base. These compounds are in general acid ammonium formates of tertiary nitrogen bases, in which the formic acid has reacted beyond the stage of classic salt formation with the tertiary nitrogen bases to give stable addition compounds bridged via hydrogen bridge bonds. These compounds can be prepared in various ways, such as (i) by direct reaction of tertiary amine with formic acid, (ii) by hydrolysis of methyl formate to form formic acid in the presence of the tertiary amine or with subsequent extraction of the hydrolysis product with the tertiary amine or (iii) by catalytic hydration of carbon monoxide or hydrogenation of carbon dioxide to form formic acid in the presence of the tertiary amine. The latter process of catalytic hydrogenation of carbon dioxide has the particular attraction that carbon dioxide is available in large quantities and is flexible in terms of source.

The fundamental work on the catalytic hydrogenation of carbon dioxide to form formic acid was carried out as early as the 1970s and 1980s. The processes of BP Chemicals Ltd. filed as the patents EP 0 095 321 A, EP 0 151 510 A and EP 0 181 078 A may be considered to result therefrom. All three documents describe the hydrogenation of carbon dioxide in the presence of a homogeneous catalyst comprising a transition metal of transition group VIII (groups 8, 9, 10), a tertiary amine and a polar solvent to form an adduct of formic acid and the tertiary amine. As preferred homogeneous catalysts, EP 0 095 321 A and EP 0 181 078 A mention ruthenium-based and EP 0 151 510 A rhodium-based complex catalysts. Preferred tertiary amines are $C_1$-$C_{10}$-trialkylamines, in particular the short-chain $C_1$-$C_4$-trialkylamines, and also cyclic and/or bridged amines such as 1,8-diazabicyclo[5.4.0]undec-7-ene, 1,4-diazabicyclo[2.2.2]octane, pyridine or picolines.

The hydrogenation is carried out at a carbon dioxide partial pressure of up to 6 MPa (60 bar), a hydrogen partial pressure of up to 25 MPa (250 bar) and a temperature from about room temperature to 200° C.

P. G. Jessop, Homogeneous Hydrogenation of Carbon Dioxide, in "The Handbook of Homogeneous Hydrogenation", Ed.: J. G. de Vries and C. J. Elsevier, Volume 1, 2007, Wiley-VCH Verlag GmbH & Co KGaA, pages 489 to 511 presents an overview on the typically used catalysts for the hydrogenation of carbon dioxide. The focus is directed to homogeneous catalysts based on elements of group VIII (groups 8, 9, 10) of the periodic table, namely Fe, Ni, Ru, Rh, Pd and Ir, but Mo and Ti are also mentioned as suitable elements.

It is crucial for an economic process that the used hydrogenation catalyst has to be removed from the product stream and recycled back into the hydrogenation reactor, because losses of catalyst would require compensation by addition of new catalyst. Another reason for the removal of the catalyst from the product stream is, that hydrogenation catalysts also catalyze the decomposition of formic acid into carbon dioxide and hydrogen, which would lead to losses of formic acid in the process. The decomposition of formic acid in the presence of hydrogenation catalysts was, for example, investigated by C. Fellay et al. and published in Chem. Eur. J. 2009, 15, pages 3752 to 3760.

WO 2010/149,507 teaches a way to solve this problem by carrying out the homogeneously catalyzed hydrogenation in the presence of a tertiary amine and a polar solvent to form two liquid phases, in which one phase is enriched with the polar solvent and the formed formic acid/amine adduct, and the other phase is enriched with tertiary amine and the homogeneous catalyst, whereby the latter one containing the homogeneous catalyst is recirculated to the hydrogenation reactor. Nevertheless, the handling of the homogeneous catalysts is a disadvantage of their use.

Heterogeneous catalysts are known to be generally much more easier separated from the reaction products. Unfortunately, neither finely devided metal particles nor conventional metal-based supported catalysts with the metals known from the homogeneous carbon dioxide hydrogenation catalysts show suitable activities and selectivities in the hydrogenation of carbon dioxide.

However, A. Baiker discloses in Appl. Organometal. Chem. 14, 2000, pages 751 to 762 the hydrogenation of carbon dioxide to formic acid derivatives in the presence of immobilized homogeneous catalysts. These specific catalysts are sythesized by functionalizing group VIII (groups 8, 9, 10) transition metal complexes, such as [Ru(PR$_3$)$_3$Cl$_2$], with bifunctional silylether-modified phosphines, like Ph$_2$P(CH$_2$)$_2$Si(OEt)$_3$ or (CH$_3$)$_2$P(CH$_2$)$_2$Si(OEt)$_3$, and reacting them with Si(OEt)$_4$ (triethoxysilan), obtaining an immobilized transition metal-based silica hydrid gel complex catalyst.

Years later, Z. Zhang et al. published in ChemSusChem 2009, 2, pages 234 to 238 the hydrogenation of carbon dioxide to a formic acid/amine adduct in the presence of 1,3-di(N,N-dimethylaminoethyl)-2-methylimidazolium trifluoromethansulfonate, as amine and ionic liquid, and a specific immobilized homogeneous Ruthenium complex catalyst. The catalyst was prepared by treating silica with (EtO)$_3$Si(CH$_2$)$_3$Cl in toluene and thioacetamide in water, reacting the resulting product with RuCl$_3$.3H$_2$O in ethanol, and mixing the formed catalyst precursor with PPh$_3$ to obtain the immobilized Ru-based complex catalyst, expressed as "Si"—(CH$_2$)$_3$NH(CSCH$_3$)—{RuCl$_3$(PPh$_3$)}.

One disadvantage of these immobilized homogeneous catalysts mentioned-above is the complex and elaborate multi step synthesis. A further disadvantage is the fact that in all these cases a polar solvent (e.g. water or an alcohol) is necessary to achieve the carbon dioxide hydrogenation. Afterwards, the polar solvent has to be removed from the formed formic acid/amine adduct which requires an additional process step and additional energy.

It was an object of the present invention to discover a process for preparing formic acid by hydrogenation of carbon dioxide, which does not have the above-mentioned disadvantages of the prior art or suffers from them only to a significantly reduced extent and allows concentrated formic acid to be obtained in a high yield and high purity. Furthermore, the process should be able to be carried out in a simple manner or at least a simpler manner than is described in the prior art, for example by means of a different, simpler process concept, simpler process stages, a reduced number of process stages or simpler apparatuses. Losses of valuable catalyst should be reduced and also the separation and recycling of the catalyst from the product phase should be simple. In addition, the process should also be able to be carried out with a low consumption of energy.

We have accordingly found a process for preparing formic acid by hydrogenation of carbon dioxide in the presence of a tertiary amine (I) and a catalyst at a pressure of from 0.2 to 30 MPa abs and a temperature of from 0 to 200° C., wherein the catalyst is a heterogeneous catalyst comprising gold.

The heterogeneous catalyst comprising gold to be used in the hydrogenation of carbon dioxide can be present in various types. In general, it can be gold itself or gold supported by a support material. In case of being gold itself, preferably gold black is used, but also other types like supported gold nanoparticles are possible. In addition, gold alloys, i.e. Au-M on supports can also be used, where M can be a precious metal like Pd or Pt as well as other kind of metals such as Ag or Cu. Also different metal promoters can be used in one and the same catalyst.

Preferably, the heterogeneous catalyst comprising gold is a supported catalyst. As support, various types of materials might be used, including but not limited to inorganic oxides, graphite, polymers or metals. In case of inorganic oxides, silicon dioxide, aluminium oxide, zirconium oxide, magnesium oxide and/or titanium oxide are preferred, but also other inorganic oxides are applicable. Particularly preferred are magnesium oxide, aluminium oxide, silica oxide, gallium oxide, zirconium oxide, ceria oxide and/or titanium oxide as support. Furthermore, mixtures of different inorganic oxides can also be used. The heterogeneous catalyst can be used in various geometric shapes and sizes, for example from powder to shaped material. In the case of a fixed-bed catalyst, use is made of, for example, pellets, cylinders, hollow cylinders, spheres, rods or extrudates. Their average particle diameter is generally from 1 to 10 mm. In case of metals or polymers as support, also meshes or knitted and crocheted wires or fabrics are applicable.

In case of a supported catalyst, the heterogeneous catalyst generally comprises 0.01 to 50 wt.-% (% by weight), preferably 0.1 to 20 wt.-% and particularly preferably 0.1 to 5 wt.-% gold, based on the total mass of the supported catalyst. In case of a non-supported catalyst, the amount of gold is generally from 0.01 to 100 wt.-%, based on the total weight of the catalyst.

Suitable heterogeneous catalysts comprising gold are commercially available or can be obtained by treatment of the support with a solution of a gold component or co-precipitation and subsequent drying, heat treatment and/or calcination by known methods.

Irrespective of whether the heterogeneous catalyst comprising gold is a supported or non-supported catalyst and irrespective of whether it additionally contains further metals (e.g. in the form of gold alloys), the heterogeneous catalyst comprising gold generally comprises gold containing particles with a diameter of 0.1 to 50 nm, measured by X-ray diffraction spectroscopy. Additionally, it may also contain particles with a diameter of less than 0.1 nm and/or more than 50 nm.

Furthermore and also irrespective of whether the heterogeneous catalyst comprising gold is a supported or non-supported catalyst and irrespective of whether it additionally contains further metals (e.g. in the form of gold alloys), the heterogeneous catalyst comprising gold generally exhibits a BET surface of $\geq 1$ m$^2$/g and $\leq 1000$ m$^2$/g, determined in accordance with DIN ISO 9277. It preferably exhibits a BET surface of $\geq 10$ m$^2$/g and $\leq 500$ m$^2$/g.

The volume of the heterogeneous catalyst comprising gold in the hydrogenation reactor is generally between 0.1 and 95% of the reactor volume, whereby the catalyst's volume is calculated by the catalyst's mass divided by its bulk density.

The tertiary amine (I) to be used in the hydrogenation of carbon dioxide in the process of the invention preferably comprises not more than 9 carbon atoms. It is preferably an amine of the general formula (Ia)

where the radicals $R^1$ to $R^3$ are identical or different and are each, independently of one another, an unbranched or branched, acyclic or cyclic or aliphatic radical having from 1 to 7 carbon atoms, preferably from 1 to 3 carbon atoms, but in total $R^1$ to $R^3$ together having not more than 9 carbon atoms, where individual carbon atoms can also be substituted, independently of one another, by a hetero group selected from the groups consisting of —O— and >N— or two or all three radicals can also be joined to one another to form a chain comprising at least four atoms in each case.

Examples of suitable tertiary amines (I) are:

Trimethylamine, N-ethyl-dimethylamine, N-propyl-dimethylamine, N-butyl-dimethylamine, N-pentyl-dimethylamine, N-hexyl-dimethylamine, N-heptyl-dimethylamine, N-methyl-diethylamine, triethylamine, N-methyl-dipropylamines (including N-methyl-di-n-propylamine, N-methyl-di-iso-propylamine and the mixed isomer N-methyl-n-propyl-iso-propylamine), N-methyl-dibutylamines (including N-methyl-di-n-butylamine, N-methyl-di-iso-butylamine, N-methyl-di-tert-butylamine and mixed isomers), tripropylamines (including tri-n-propylamine, tri-iso-propylamine and mixed isomers), N-ethyl-dipropylamines (including N-ethyl-di-n-propylamine, N-ethyl-di-iso-propylamine and the mixed isomer), N-butyl-diethylamines (including N-n-butyl-diethylamine, N-iso-butyl-diethylamine, N-tert-butyl-diethylamine and mixed isomers).

N-Methyl-pyrrolidine, N-ethyl-pyrrolidine, N-propyl-pyrrolidine (including N-n-propyl-pyrrolidine and N-iso-propyl-pyrrolidine), N-butyl-pyrrolidine (including N-n-butyl-pyrrolidine, N-iso-butyl-pyrrolidine and N-tert-butyl-pyrrolidine).

N-Methyl-piperidine, N-ethyl-piperidine, N-propyl-piperidine (including N-n-propyl-piperidine and N-iso-propyl-piperidine).

N,N-dimethyl-cyclohexylamine, N,N-dimethyl-cyclopentylamine, N,N-diethyl-cyclopentylamine.

In case of the possibility of isomers of the tertiary amines (I) mentioned above, all of the isomers shall be included by the name of the generic terms.

It is naturally also possible to use mixtures of various tertiary amines (I) in the process of the invention.

In the process of the invention, particular preference is given to using a saturated amine of the general formula (Ia) and more particularly preferred a saturated amine (Ia) in which the radicals $R^1$ to $R^3$ are selected independently from the group consisting of $C_1$-$C_7$-alkyl and $C_5$-$C_6$-cycloalky, but in total $R^1$ to $R^3$ together having not more than 9 carbon atoms.

Very particular preference is given to using an amine of the general formula (Ia) in which the radicals $R^1$ to $R^3$ are selected independently from the group consisting of $C_1$-$C_3$-alkyl. In particular the tertiary amine (I) is trimethylamine, triethylamine and/or a tripropylamine, whereby trimethylamine, triethylamine and tri-n-propylamine are particularly preferred.

The amount of the tertiary amine (I) to be used in the hydrogenation process of the invention is generally from 0.05 to 0.99 mL tertiary amine (I) per mL of the total reactor volume and preferably from 0.2 to 0.95 mL tertiary amine (I) per mL of the total reactor volume, whereby the volume of the tertiary amine (I) is based on the volume of the liquid tertiary amine (I) it would have as pure substance under reaction conditions.

The carbon dioxide to be used in the hydrogenation of carbon dioxide can be used in solid, liquid or gaseous form. It is also possible to use industrially available gas mixtures comprising carbon dioxide. The hydrogen to be used in the hydrogenation of carbon dioxide is generally gaseous. Carbon dioxide and hydrogen can also comprise inert gases such as nitrogen or noble gases, but surprisingly, the gold catalysts are also tolerating carbon monoxide, which is a catalyst poison when using the standard ruthenium catalysts for this reaction. However, the content of these gases, especially carbon monoxide, should not exceed 20 mol-% based on the total amount of carbon dioxide and hydrogen in the hydrogenation reactor. Although larger amounts may likewise be tolerable, they generally require the use of higher pressure in the reactor which in turn makes further compression energy necessary.

The hydrogenation of carbon dioxide is carried out in the liquid phase at a temperature of from 0 to 200° C. and a total pressure of from 0.2 to 30 MPa abs. The temperature is preferably at least 20° C. and particularly preferably at least 30° C. Preferably, it is not more than 100° C. The total pressure is preferably at least 1 MPa abs and particularly preferably at least 5 MPa and also generally not more than 25 MPa abs and preferably not more than 20 MPa abs.

The molar ratio of hydrogen to carbon dioxide in the feed to the hydrogenation reactor is preferably from 0.1 to 10 and particularly preferably from 1 to 3.

The molar ratio of carbon dioxide to tertiary amine (I) in the feed to the hydrogenation reactor is generally from 0.1 to 20 and preferably from 0.5 to 3.

The hydrogenation can be carried out in the presence or in the absence of a further solvent. As solvents, unpolar as well as polar solvents can be added. In case of polar solvents, like alcohols or water, their amount is generally and advantageously less than 20 wt.-% of the amount of tertiary amine (I).

As hydrogenation reactors, it is in principle possible to use all reactors which are suitable in principle for heterogeneously catalyzed gas/liquid reactions at the given temperature and the given pressure. Suitable standard reactors for the hydrogenation are indicated, for example, in K. D. Henkel, "Reactor Types and Their industrial Applications", in Ullmann's Encyclopedia of Industrial Chemistry, 2005, Wiley-VCH Verlag GmbH&Co. KGaA, DOI: 10.1002/14356007.b04_087. Examples which may be mentioned are stirred tank reactors, tubular reactors, multi-tubular reactors, multi-channel reactors, micro-channel reactors or fixed bed reactors.

The hydrogenation of carbon dioxide in the process of the invention can be carried out batchwise or continuously. In the case of batch operation, the reactor is typically charged with the heterogeneous catalyst and the desired tertiary amine (I), and carbon dioxide and hydrogen subsequently introduced to the desired pressure at the desired temperature. After the hydrogenation, the reactor is generally depressurized and the liquid reaction mixture separated from the heterogeneous catalyst.

In the continuous mode of operation, the tertiary amine (I), carbon dioxide and hydrogen are introduced continuously. However, if a fixed-bed heterogeneous catalyst is used, it is generally present beforehand in fixed form in the reactor. In case of a suspended heterogeneous catalyst, it normally might also be present in the reactor beforehand or be introduced in an amount equal to that of its removal by the continuous reactor discharge. Accordingly, the liquid reaction mixture is continuously discharged from the reactor so that the average liquid level in the reactor remains constant. Preference is given to the continuous hydrogenation of carbon dioxide.

Irrespective of the type of the heterogeneous catalyst and whether the hydrogenation is performed batchwise or continuously, the liquid reaction mixture is after the hydrogenation reaction generally separated from the heterogeneous catalyst. In case of using a fixed-bed catalyst, it normally stays in the reactor when the reaction mixture is discharged, due to its immobilization. In case of using a non-immobilized heterogeneous catalyst, it is typically either kept back in the reactor by common precautions (e.g. by a mesh or a filter at the outlet) or separated from the reaction mixture by simple filtration, decantation or centrifugation and recycled back to the hydrogenation reactor. After the separation of the catalyst, the liquid reaction mixture is practically free of gold, which means 1 wt.-ppm of gold or less in the separated reaction mixture.

The average residence time in the reactor is generally from 10 minutes to 10 hours.

The obtained liquid product mixture comprising formic acid and the tertiary amine (I) generally contains formic acid and the tertiary amine (I) in form of a formic acid/amine adduct. If a tertiary amine of formula (Ia) was used, the formic acid/amine adduct usually has the general formula (III)

$$xHCOOH*NR^1R^2R^3 \quad (III)$$

where the radicals $R^1$ to $R^2$ are the radicals described for the tertiary amine (Ia) and x is from 0.5 to 5, preferably from 1.2 to 2.6. The factor x can be determined, for example by titration with KOH solution against phenolphthalein. The precise composition of the formic acid/amine adduct (III) depends on many parameters, for example the prevailing concentrations of formic acid and tertiary amine (Ia), pressure, temperature or the presence and nature of further components, in particular of polar solvents if present. The composition of the formic acid/amine adduct (III) can therefore also change over the individual process steps in which the formic acid/amine adduct (III) is in each case referred to in the present patent application. The composition of the formic acid/amine adduct (III) can easily be determined in each process step by determining the formic acid content by acid-base titration and determining the amine content by gas chromatography.

The product mixture obtained by the hydrogenation comprising formic acid and the tertiary amine (I) is then preferably subjected to a base exchange and for this preferably reacted with a tertiary amine (II) which comprises 12 to 48 carbon atoms, the released tertiary amine (I) preferably separated whereby a product mixture comprising formic acid and tertiary amine (II) is obtained, and the formic acid preferably removed from said product mixture by distillation. It is known from the prior art and for example mentioned in EP 0 357 243 A, EP 0 181 078 A or EP 0 597 151 A that a base exchange of the formic acid/amine adduct with a higher boiling amine base is advantageous for obtaining an adduct which then can be thermally dissociated into free formic acid and free tertiary amine and the free formic acid being recovered by distillation.

The tertiary amine (II) to be reacted with the product mixture obtained by the hydrogenation preferably has, at a pressure of 1013 hPa abs, a boiling point which is at least 10° C. higher, particularly preferably at leas 50° C. higher and very particularly preferably at least 100° C. higher, than that of formic acid. A restriction in terms of an upper limit to the boiling point is not necessary since a very low vapor pressure of the tertiary amine (II) is in principle an advantage for the process of the invention. In general, the boiling point of the tertiary amine (II) at a pressure of 1013 hPa abs, if necessary at a pressure extrapolated by known methods from vacuum to 1013 hPa abs, is below 500° C.

The tertiary amine (II) which is preferably reacted with the product mixture obtained by the hydrogenation is preferably an amine of the general formula (IIa)

$NR^1R^2R^3$ (IIa)

where the radicals $R^1$ to $R^3$ are identical or different and are each, independently of one another, an unbranched or branched, acyclic or cyclic, aliphatic, araliphatic or aromatic radical having from 1 to 46 carbon atoms, preferably from 1 to 18 carbon atoms, but in total $R^1$ to $R^3$ together having at least 12 carbon atoms and not more than 48 carbon atoms, where individual carbon atoms can also be substituted, independently of one another, by a hetero group selected from the groups consisting of —O— and >N— or two or all three radicals can also be joined to one another to form a chain comprising at least four atoms in each case. Preference is given to at least one of the radicals bearing two hydrogen atoms on the alpha-carbon atom.

Examples of suitable tertiary amines (II) are:
Tributylamines (including tri-n-butylamine, tri-iso-butylamine and mixed isomers), tripentylamines (including tri-n-pentylamine and all other isomers), trihexylamines (including tri-n-hexylamine and all other isomers), triheptylamines (including tri-n-heptylamine and all other isomers), trioctylamines (including tri-n-octylamine and all other isomers), trinonylamines (including tri-n-nonylamine and all other isomers), tridecylamines (including tri-n-decylamine and all other isomers), tridodecylamine (including tri-n-dodecylamine and all other isomers), tritetradecylamines (including tri-n-tetradecylamine and all other isomers), tripentadecylamine (including tri-n-pentadecylamine and all other isomers), trihexadecyclamine (including tri-n-hexadecylamine and all other isomers), tri(2-ethyl-n-hexyl)amine, N-dimethyl-decylamine (including N-dimethyl-n-decylamine and all other isomers), N-dimethyl-dodecylamine (including N-dimethyl-n-dodecylamine and all other isomers), N-dimethyl-tetradecylamine (including N-dimethyl-n-tetradecylamine and all other isomers), N-dioctyl-methylamine (including N-di-n-octyl-methylamine and all other isomers), N-dihexyl-methylamine (including N-dihexyl-methylamine and all other isomers), tricyclopentylamine, tricyclohexylamine, tricyclooctylamine and derivates thereof which are substituted by one or more methyl, ethyl, 1-propyl, 2-propyl, 1-butyl, 2-butyl or 2-methyl-2-propyl groups.
N-Dimethylcyclohexylamine, N-methyl-dicyclohexylamine, N-diethyl-cylcohexylamine, N-ethyldicyclohexylamine.
Triphenylamine, N-methyldiphenylamine, N-ethyldiphenylamine, N-propyldiphenylamine, N-butyladiphenylamine, N-2-ethylhexyldiphenylamine, N-dipropylphenylamine, N-dibutylphenylamine, N-bis(2-ethylhexyl)phenylamine, tribenzylamine, N-methyldibenzylamine, N-ethyldibenzylamine and derivates thereof which are substituted by one or more methyl, ethyl, 1-propyl, 2-propyl, 1-butyl, 2-butyl or 2-methyl-2-propyl groups.
N—$C_6$-$C_{18}$-alkylpiperidines, N,N-di-$C_1$-$C_{18}$-alkylpiperazines, N—$C_7$-$C_{18}$-alkylpyrollidines, N—$C_8$-$C_{24}$-alkylimidazoles and derivates thereof which are substituted by one or more methyl, ethyl, 1-propyl, 2-propyl, 1-butyl, 2-butyl or 2-methyl-2-propyl groups.

In case of the possibility of isomers of the tertiary amines (II) mentioned above, all of the isomers shall be included by the name of the generic terms.

It is naturally also possible to use mixtures of various tertiary amines (II) in the process of the invention.

In the process of the invention, particular preference is given to using a saturated amine of the general formula (IIa) and more particularly preferred a saturated amine (IIa) in which the radicals $R^1$ to $R^3$ are selected independently from the group consisting of $C_1$-$C_{18}$-alkyl and $C_5$-$C_8$-cycloalkyl but in total $R^1$ to $R^3$ together having at least 12 carbon atoms and not more than 32 carbon atoms.

Very particular preference is given to using an amine of the general formula (IIa) in which the radicals $R^1$ to $R^3$ are selected independently from the group consisting $C_5$-$C_8$-alkyl. In particular the tertiary amine (II) is a tri-n-pentylamine, a trihexylamine, a triheptylamine, a trioctylamine, N-methyldicyclohexylamine, a N-dioctylmethylamine and/or a N-dimethyldecylamine, whereby tri-n-pentylamine, tri-n-hexylamine, tri-n-heptylamine, tri-n-octylamine, N-methyldi-n-cyclohexylamine, N-di-n-octylmethylamine and N-dimethyl-n-decylamine are particularly preferred.

The amount of the tertiary amine (II) to be used in the reaction with the product mixture obtained by the hydrogenation is generally from 5 to 95 wt.-% and preferably from 10 to 90 wt.-%, based on the amount of tertiary amine (I) in the product mixture (including free tertiary amine (I) and tertiary amine (I) bound in the adduct).

The reaction of the tertiary amine (II) with the product mixture obtained by the hydrogenation is carried out in the liquid phase at a temperature of generally from 20 to 200° C. and a total pressure of from 0.01 to 20 MPa abs. The temperature is preferably at least 50° C. and also preferably not more than 150° C. The total pressure is preferably at least 0.05 MPa abs and also generally not more than 10 MPa abs.

As reactors for the base exchange, it is in principle possible to use all reactors which are suitable in principle for liquid/liquid reactions at the given temperature and the given pressure. Suitable standard reactors for the base exchange are indicated, for example, in K. D. Henkel, "Reactor Types and Their industrial Applications", in Ullmann's Encyclopedia of Industrial Chemistry, 2005, Wiley-VCH Verlag GmbH & Co. KGaA, DOI: 10.1002/14356007.b04_087. Examples which may be mentioned are stirred tank reactors, tube reactors or distillation columns.

Irrespective of the type of reactor for the base exchange, the released tertiary amine (I) is then separated whereby a product mixture comprising formic acid and the tertiary amine (II) is obtained. The separation is generally performed by distilling off the released tertiary amine (I), but also other methods may be suitable, as for example separation by diaphragm. Preferably, the released tertiary amine (I) is separated by distillation. The removal of the tertiary amine (I) can take place in the same apparatus used for the base exchange (e.g. a distillation column or a stirred tank reactor) or in a separate apparatus.

The tertiary amine (I), which is released by the reaction of the product mixture comprising formic acid and tertiary amine (I) with tertiary amine (II) and separated, is advantageously recycled to the step of the hydrogenation. In general, from 10 to 100%, preferably from 50 to 100%, particularly preferably from 80 to 100%, very particularly preferably from 90 to 100% and in particular from 95 to 100% of the separated tertiary amine (I) is recycled to the step of the hydrogenation.

The base exchange can be carried out batchwise or continuously.

The obtained liquid product mixture comprising formic acid and the tertiary amine (II) generally contains formic acid and the tertiary amine (II) in form of a formic acid/amine adduct. If a tertiary amine of formula (IIa) was used, the formic acid/amine adduct usually has the general formula (IV)

$$xHCOOH*NR^1R^2R^3 \quad (IV)$$

where the radicals $R^1$ to $R^2$ are the radicals described for the tertiary amine (IIa) and x is from 0.5 to 5, preferably from 1.2 to 2.6, The factor x can be determined, for example by titration with KOH solution against phenolphthalein. The precise composition of the formic acid/amine adduct (IV) depends on many parameters, for example the prevailing concentrations of formic acid and tertiary amine (IIa), pressure, temperature or the presence and nature of further components, in particular of polar solvents if present. The composition of the formic acid/amine adduct (IV) can therefore also change over the individual process steps in which the formic acid/amine adduct (IV) is in each case referred to in the present patent application. The composition of the formic acid/amine adduct (IV) can easily be determined in each process step by determining the formic acid content by acid-base titration and determining the amine content by gas chromatography.

The obtained liquid product mixture comprising formic acid and the tertiary amine (II) is then subjected to distillation in which formic acid is released from the formic acid/amine adduct by thermal dissociation and removed. This step can generally be carried out under process parameter known in the prior art for the thermal dissociation of formic acid/amine adducts into free formic acid and the respective amine and, for example, described in EP 0 181 078 A or WO 2006/021,411.

The distillation apparatus generally comprises, in addition to the actual column body with internals, inter alia a top condenser and a bottom evaporator. In addition, this may optionally also comprise still further peripheral apparatuses or internals and, for example, a flash container in the feed (for example for separating gas and liquid in the feed to the column body), an intermediate evaporator (for example for improved heat integration of the process) or internals for avoiding or reducing aerosol formation (such as, for example, thermostatable trays, demisters, coalescers or deep-bed diffusion filters). The column body may be equipped, for example, with structured packings, random packings or trays. The number of separation stages required is dependent in particular on the type of tertiary amine (II), the concentration of formic acid and tertiary amine (II) in the product mixture fed to the distillation apparatus and the desired concentration or the desired purity of the formic acid and can be determined by the person skilled in the art in the customary manner. In general, the number of required separation stages is ≥3, preferably ≥6 and particularly preferably ≥7. There are in principle no upper limits. For practical reasons, however, it is likely to be customary to use as a rule ≤50, optionally ≤30, separation stages.

The product mixture can be fed to the distillation apparatus, for example, as a side stream to the column body.

Optionally, the addition can also be effected upstream of a flash evaporator, for example. In order to keep the thermal load on the feed stream in the distillation apparatus as low as possible, it is generally advantageous rather to feed this to the lower region of the distillation apparatus. Thus, it is preferable to feed in the product mixture in the region of the lower fourth, preferably in the region of the lower fifth and particularly preferably in the region of the lower sixth of the available separation stages, a direct feed into the bottom of course also being included here.

Alternatively, however, it is also preferable to feed said product mixture to the bottom evaporator of the distillation apparatus.

The distillation apparatus is generally operated at a bottom temperature of from 100 to 300° C. and a pressure of from 30 to 3000 hPa abs. Preferably, the distillation apparatus is operated at a bottom temperature of ≥120° C., particularly preferably of ≥140° C. and preferably of ≥220° C. and particularly preferably of ≤200° C. The pressure is preferably ≥30 hPa abs, particularly preferably ≥60 hPa abs and preferably ≤1500 hPa abs and particularly preferably ≤500 hPa abs.

The formic acid released by the thermal dissociation can be obtained as top product and/or side product from the distillation apparatus. When the product mixture comprises constituents boiling lower than formic acid, it may be advantageous to separate these off by distillation as top product and the formic acid in the side take-off. Where gases may be dissolved in the product mixture (such as, for example, carbon monoxide or carbon dioxide), however, it is as a rule also possible to separate off the formic acid together with these as top product. If the product mixture comprises constituents boiling higher than formic acid, formic acid is preferably separated off by distillation as top product, but optionally instead of these or in addition in the form of a second stream in the side take-off. The constituents boiling higher than formic acid are in this case then preferably taken off via an additional side stream.

In this way, formic acid having a content of up to 100 wt.-% can be obtained. In general, formic acid contents of from 75 to 99.995 wt.-% are achievable without problems. The residual content to 100 wt.-% might, for example, be water added to the hydrogenation of carbon dioxide to promote the heterogeneously catalyzed reaction. Thus, water may already be present in the product mixture fed to the distillation apparatus but may optionally also form only during the thermal separation in small amounts as a result of decomposition of formic acid itself.

In the recovery of concentrated formic acid having a content from 95 to 100 wt.-% as bottom or side product, water is discharged with a part of the eliminated formic acid in a side stream. The formic acid content of this side stream is typically from 75 to 95 wt.-%. However, it is also possible to discharge the water and the eliminated formic acid in a common top or side stream. The formic acid content of the product thus obtained is then as a rule from 85 to 95 wt.-%.

The formic acid obtainable by the process according to the invention has a low color number and a high color number stability. In general, a color number of ≤20 APHA and in particular even of ≤10 APHA and optionally even of ≤5 APHA can be achieved without problems. Even on storage for several weeks, the color number remains virtually constant or increases only insignificantly.

The bottom product obtained in the step of the removal of formic acid by distillation and containing tertiary amine (II) is advantageously recycled to the step of the reaction of the product mixture comprising formic acid and tertiary amine (I) with tertiary amine (II) (base exchange). In general, from 10 to 100%, preferably from 50 to 100%, particularly preferably from 80 to 100%, very particularly preferably from 90 to 100% and in particular from 95 to 100% of the tertiary amine (II) of the bottom product is recycled to the step of the hydrogenation.

The bottom product taken off from the distillation unit can still comprise small residual amounts of formic acid, but the molar ratio of formic acid to tertiary amine (I) is preferably 0.1 and particularly preferably 0.05.

DE 34 28 319 A has described the thermal dissociation of an adduct of formic acid and a tertiary amine having $C_6$-$C_{14}$-alkyl radicals in a dissociation column. Likewise, WO 2006/021,411 also describes the thermal dissociation of an adduct of formic acid and a tertiary amine having a boiling point at atmospheric pressure of from 105 to 175° C. in a dissociation column. EP 0 563 831 A similarly discloses the thermal dissociation of an adduct of formic acid and a tertiary amine having a boiling point higher than that of formic acid, with added formamide being said to give a particularly color-stable formic acid.

Figure 1:
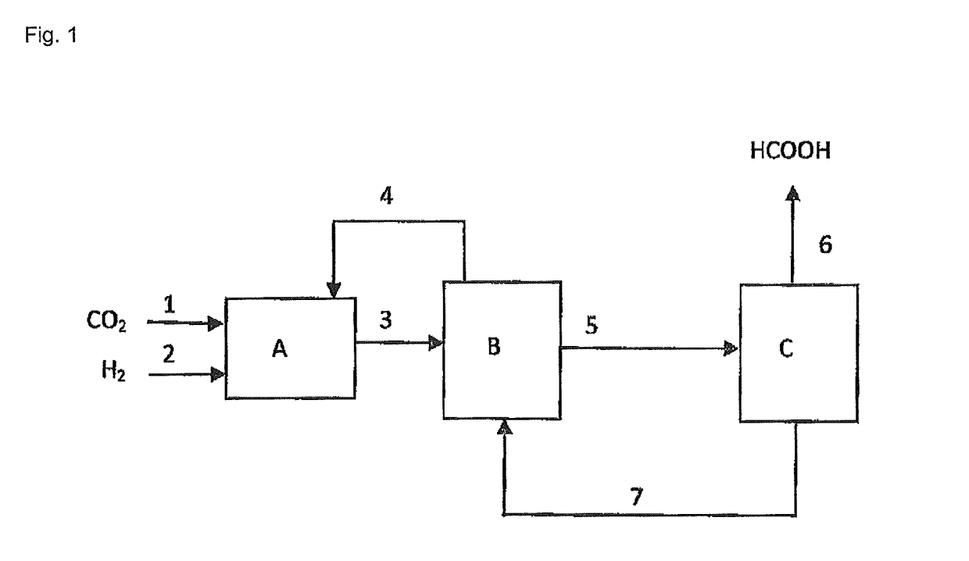
FIG. 1 is a schematic block diagram of a possible embodiment of the process of the invention. The individual letters have the following meanings: A=hydrogenation reactor; B=base exchange unit; C=distillation unit.

FIG. 1 shows a schematic block diagram of a possible embodiment of the process of the invention. Here, the individual letters have the following meanings:
A=hydrogenation reactor
B=base exchange unit
C=distillation unit Carbon dioxide and hydrogen are fed into the hydrogenation reactor "A". In this reactor, the carbon dioxide and hydrogen are reacted in the presence of a heterogeneous catalyst comprising gold and a tertiary amine (I) comprising not more than 9 carbon atoms to form a product mixture comprising formic acid and tertiary amine (I). The obtained product mixture is fed to a base exchange unit "B" in which it is reacted with a tertiary amine (II) comprising 12 to 32 carbon atoms. Thereby, tertiary amine (I) is released and separated from the obtained product mixture comprising formic acid and tertiary amine (II). The released and separated tertiary amine (I) is then preferably recycled back to the hydrogenation reactor "A". The obtained product mixture comprising formic acid and tertiary amine (II) is fed to the distillation unit "C" and the formic acid/amine adduct is thermally dissociated therein into free formic acid and tertiary amine (II). The free formic acid is, for example, removed as overhead product. The bottoms from the distillation unit "C" are preferably recycled to the base exchange unit "B".

It is of course possible to supplement the process of the invention by further process steps or inflows or outflows of streams if required.

The process of the invention makes it possible to obtain concentrated formic acid in high yield and high purity by hydrogenation of carbon dioxide. In particular, it provides a particularly simple and elegant mode of operation which compared to the prior art has a simpler process concept, simpler process stages, a smaller number of process stages and simpler apparatuses. Thus, for example, the heterogeneous catalyst comprising gold can be very easily completely separated from the product solution by simple operation like filtration, decantation or centrifugation or can be used as a fixed bed catalyst. Losses of catalyst and thus losses of gold are minimized by the retention of the catalyst in the reactor. The simpler process concept makes it possible for the production plant required for carrying out the process of the invention to be made more compact in sense of a smaller space requirement and the use of fewer apparatuses compared to the prior art. It has lower capital cost requirements and a lower energy consumption.

EXAMPLES

Materials

Unless stated otherwise, the following specific materials were used.
a) Light MgO:
    Apparent density 103.45 g/L. Supplied by A.C.E.F. s.p.a.
b) AUROlite™ Au/$TiO_2$:
    1.0±0.1 wt.-% Au on $TiO_2$ extrudates of 1.5 mm diameter and an average length of 5 mm, bulk density 0.85-0.95 g/mL, BET surface 40-50 m2/g. Supplied by Strem Chemicals Inc. Used as received.

Methods
Unless stated otherwise, the following methods were employed.
a) AAR:
    The molar acid/amine-ratio AAR of the HCOOH/$NEt_3$-adducts were determined by NRM in $D_2O$.
b) Amounts of transferred gases:
    The amounts of gases transferred under pressure were determined by balancing the weight of the respective apparatus (e.g. reactor or reservoir).
c) Reservoir:
    As reservoirs for high-pressure gases two interchangeable, magnetically stirred autoclaves with an internal volume of 410 mL each were used.
d) Determination of the gas ratios:
    The molar $H_2$/$CO_2$/CO/Ar gas ratios were determined by passing a gas sample through a weighed soda lime cartridge and analyzing the residual gas by gas chromatography.
e) Analysis of CO contents lower than 0.2 mol-% in $H_2$/$CO_2$ mixtures:
    CO contents lower than 0.2 mol-% in $H_2$/$CO_2$ mixtures were analyzed by passing a gas sample through a (i) minus 23° C. cooling trap (to condense readily condensable compounds such as water, formic acid or triethylamine), (ii) a weighted soda lime cartridge (to absorb the $CO_2$), (iii) a minus 80° C. cooling trap (to condense water), and (iv) a NDIR-CO analyzer. The remaining gas sample was collected in a gasometer.
f) Analysis of Au:
    Au was analyzed by inductively coupled plasma (ICP).

Example 1

Preparation of Gold(III) Hydroxide 100 mL of a $HAuCl_4$ solution containing 20 g (101 mmol) of Au were added dropwise into 54 G (1.35 mol) of light MgO suspended in 350 mL of water and stirred during 12 hours. The resulting pale yellow Au$(OH)_3$/MgO co-precipitate was collected on a filter and washed with water until negative chloride test (moist Au$(OH)_3$/MgO co-precipitate). The solid was suspended in 400 mL of water and the milky, stirred suspension treated dropwise with 155 mL of 10 M $H_2SO_4$. An orange precipitate was formed, which was collected on a filter, repeatedly rinsed with water and then squeezed, whereas the MgO dissolved in the $H_2SO_4$. The isolated squeezed filter cake contained 15 wt.-% Au.

Example 2

Preparation of Gold Black GB 1

6.5 g of freshly prepared squeezed gold(III) hydroxide of Example 1 (referring to 5 mmol Au) was stirred in 300 mL of water until an orange suspension free of lumps was obtained. The suspension was cooled at 5° C. with ice cubes and a freshly prepared mixture of 1.8 mL of 37 wt.-% formaldehyde (referring to 22 mmol formaldehyde) in a solution of 1.2 g NaOH in 50 mL of water (referring to 30 mmol NaOH) was added in a single portion while shaking the flask. After a short induction period, a vigorous hydrogen evolution accompanied the formation of a black voluminous solid which was collected on a filter, washed with water and dried under vacuum. 1 g of gold black GB 1 with a gold content of 99.95 wt.-% was obtained (referring to 5 mmol of Au).

Example 3

Preparation of Au/MgO

Moist $Au(OH)_3$/MgO co-precipitate prepared from 101 mmol of Au as described in Example 1 was suspended in 500 mL of water and magnetically stirred to form a suspension free of lumps. To the stirred suspension 32 mL of 37 wt.-% formaldehyde (referring to 395 mmol formaldehyde) were added at room temperature. The reduction was accompanied by hydrogen evolution. The indigo-colored solid was collected on a filter, washed with water and dried under vacuum. 75 g of 26 wt.-% Au/MgO were obtained (referring to an Au-content of 26 wt.-% of the total mass of the supported Au/MgO-catalyst).

Example 4

Preparation of Gold Black GB 2

3.88 g of Au/MgO prepared in accordance with Example 3 and having an Au-content of 1.0 g (referring to 5 mmol) were suspended into 30 mL of 1.33 $HCOOH/NEt_3$-adduct (AAR=1.33). A smooth gas evolution occurred. After 1 hour the adduct was, together with some $NEt_3$ at the surface, siphoned off and the residue washed with a fresh 30 mL portion of the 1.33 $HCOOH/NEt_3$-adduct. The washing was repeated twice more and the gold black GB 2 was obtained as a voluminous solid swimming in the adduct. For analytical reasons a small portion was collected on a filter, washed with water and dried under vacuum. The residual amount of Mg in GB 2 was 500 wt-ppm.

Example 5

Decomposition of Adduct in the Presence of GB 2

Figure 2:
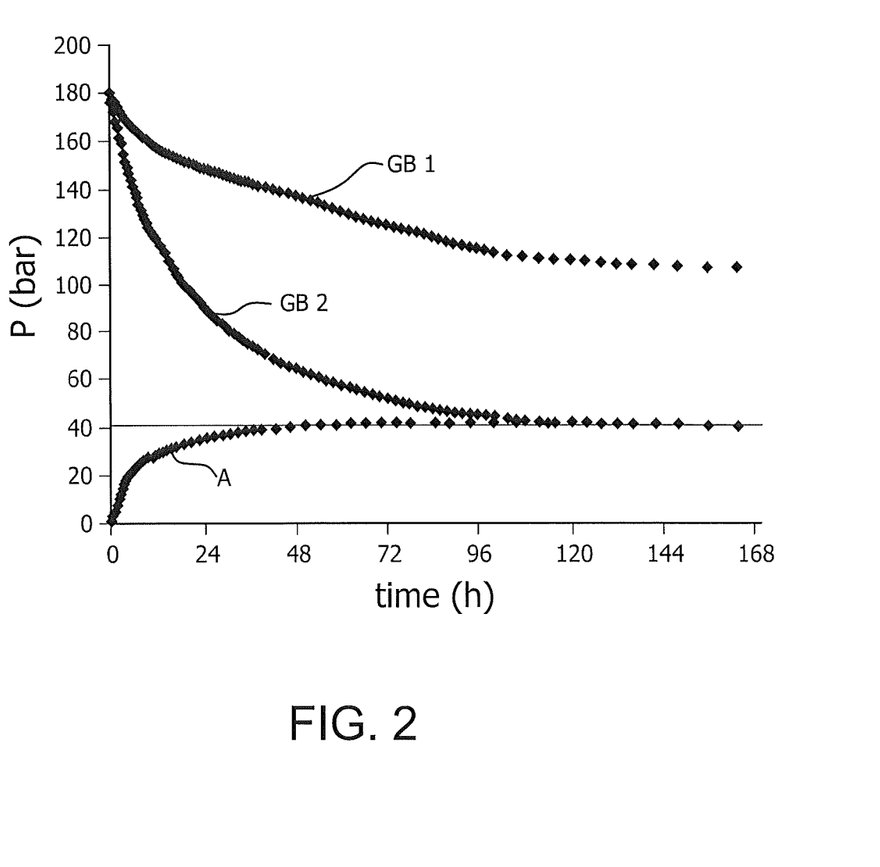
FIG. 2 represents pressure/time curves for Examples 5, 7, and 8. The individual letters have the following meanings: A represents Example 5; GB 1 represents Example 7; GB 2 represents Example 8.

Comparative Example 1 g of GB 2 and 50 mL (300 mmol) of the 1.33 $HCOOH/NEt_3$-adduct (AAR=1.33) were introduced in a rocking stainless-steel autoclave with an internal volume of 120 mL and heated at 40° C. in a water bath. The pressure/time curve is shown as curve "A" in FIG. 2. After approximately 2 days a constant pressure of about 4.1 PMa abs was obtained due to the decomposition of adduct into $H_2$, $CO_2$ and $NEt_3$. After 132 hours the autoclave was cooled in ice/water and depressurized. The off-gas contained 3.8 g (86 mmol) of $CO_2$, 174 mg (87 mmol) of $H_2$ and 11 mg (0.4 mmol) of CO. The liquid was poured into a graduated cylinder and the amounts of free amine and the immiscible 1.33 $HCOOH/NEt_3$-adduct (AAR=1.33) were determined by the volume of their phases, based on their densities ($\rho(NEt_3)$=0.725 g/mL and $\rho$(1.33 adduct)=0.975 g/mL at 20° C.). 8.8 mL (63 mmol) of $NEt_3$ and 39.5 mL (237 mmol) of 1.33 $HCOOH/NEt_3$-adduct (AAR=1.33) were recovered.

Example 6

Comparison of a Group VIII Hydrogenation Catalyst Under Similar Conditions 5 g of a Re—Ru-hydrogenation catalyst (on $Al_2O_3$; 0.5 wt.-% Ru, 0.5 wt.-% Re) and 100 g of $NEt_3$ were introduced in a stirred Hastolloy C autoclave with an internal volume of 270 mL, pressurized with 30 g of $CO_2$ (2.1 MPa abs) and up to 20.0 MPa abs with $H_2$. The autoclave was heated for 10 hours at 55° C. After this time, the autoclave was depressurized and the liquid product was poured into a separation funnel. Only one liquid phase was formed, which was nearly pure $NEt_3$. No formic acid was formed.

Examples 7 and 8

Production of Adduct (According to the Invention)

1 g of GB 1 (Ex. 7) or GB 2 (Ex. 8), respectively, 10 mL (60 mmol) of the 1.33 $HCOOH/NEt_3$-adduct (AAR=1.33) and 40 mL (286 mmol) of $NEt_3$ were introduced in a, rocking stainless-steel autoclave with an internal volume of 120 mL, pressurized with 14 g of $H_2/CO_2$ 1:1 mixture (304 mmol each) and heated at 40° C. in a water bath. A total pressure of 18 MPa abs was attained. The pressure/time curves are shown as curve "GB 1" for Example 7 and "GB 2" for Example 8 in FIG. 2. After 160 hours the autoclave was cooled in ice/water and depressurized. The liquid product was poured into a graduated cylinder and the amounts of free amine and the immiscible 1.33 adduct were determined by the volume of their phases, based on their densities ($\rho(NEt_3)$=0.725 g/mL and $\rho$(1.33 adduct)=0.975 g/mL at 20° C.). The 10 mL of the 1.33 adduct added to the batch were of course subtracted in the calculation of the produced amount. The mass balances are shown in Table 1.

The experiments show that both gold catalysts GB 1 and GB 2 produced a respectable amounts of 1.33 $HCOOH/NEt_3$-adduct. GB 1 afforded a yield of approx. 35% (80 mmol×1.33/304) and GB 2 of approx. 71% (163 mmol×1.33/304 mmol) formic acid bound in the 1.33 $HCOOH/NEt_3$-adduct with regard to the amounts of introduced $H_2$ and $CO_2$.

Example 9

Production of Adduct (According to the Invention)

The continuous production of adduct was carried out in a magnetically driven PARR autoclave with an internal volume of 320 mL equipped with temperature and pressure sensors and with a dip tube carrying a 160 mesh steel net at its internal tip. The autoclave was connected with thin, wound up capillary tubes to a high pressure reservoir filled with a $H_2/CO_2$ 1:1 mixture, to a reservoir of supercritical $CO_2$ kept at 80° C. at 14 MPa abs and to a HPLC pump for the supply with $NEt_3$. The amounts of the introduced gases were determined by weighing the reservoirs and the amount of introduced $NEt_3$ was determined by volume.

Figure 3:
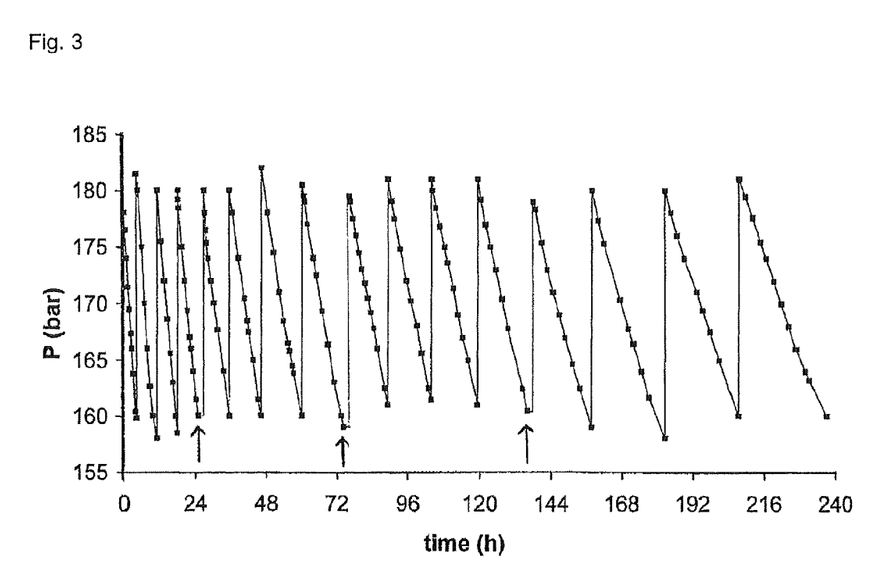
FIG. 3 represents a pressure/time curve based on the continuous production of adduct of Example 9. The arrows represent a short interruption in stirring to allow the HCOOH/NEt$_3$-adduct to separate.

The autoclave was charged with 2 g of GB 2 (Ex. 8) suspended in 35 mL (210 mmol) of 1.33 HCOOH/NEt$_3$-adduct (AAR=1.33), 100 mL (715 mmol) of NEt$_3$ and pressurized with 41.7 g of H$_2$/CO$_2$ 1:1 mixture (referring to 906 mmol of H$_2$ and CO$_2$ each), The autoclave was then heated at 40° C. by a heater and a starting pressure of 17.8 MPa abs was attained. As shown in FIG. 3, the pressure slightly decreased with time. After having reached 16.0 MPa abs, 18.2 MPa abs were restored by adding further H$_2$/CO$_2$ 1:1 mixture (about 4 g, referring to 87 mmol of H$_2$ and CO$_2$ each). The pressure slightly decreased again. After having fallen below 16 MPa abs, further H$_2$/CO$_2$ 1:1 mixture was introduced. This procedure was repeated again.

After the fourth pressure decrease to about 16 MPa abs, the stirring was shortly interrupted to allow the HCOOH/NEt$_3$-adduct to separate. In FIG. 3, the interruption is illustrated by an arrow. 50 mL of clean, colourless, gold free, liquid 1.33 HCOOH/NEt$_3$-adduct (AAR=1.33) were withdrawn from the bottom of the autoclave through the dip tube. The withdrawn amount was depressurized and analyzed. It contained about 300 mmol of 1.33 HCOOH/NEt$_3$-adduct (AAR=1.33), 7 g (159 mmol) of CO$_2$ and 10 mg (5 mmol) of H$_2$. The small amount of the withdrawn H$_2$ was neglected while the amount of the withdrawn CO$_2$ was reintroduced into the autoclave from a reservoir charged with liquid CO$_2$, which was warmed up to 80° C. Then, 42 mL (300 mmol) of NEt$_3$ were introduced into the autoclave with the HPLC pump while the stirring was started again. Afterwards, a pressure of about 18 MPa abs was restored by adding further H$_2$/CO$_2$ 1:1 mixture.

The procedures were repeated several times as shown in FIG. 3 and stopped after about 240 hours of operation. A total of 216 mL (1.3 mol) of the 1.33 HCOOH/NEt$_3$-adduct (AAR=1.33) were formed. In total, about 14 mmol of CO were determined in all the gases released.

The experiment shows a significant production of the 1.33 HCOOH/NEt$_3$-adduct over a time of about 240 hours. Gold black GB 2 afforded a yield of formic acid of approx. 71% (1.3 mol×1.33/2.44 mol) bound in the 1.33 HCOOH/NEt$_3$-adduct with regard to the amounts of introduced H$_2$ and CO$_2$.

Examples 10 and 11

Influence of CO and Ar to Production of Adduct (According to the Invention)

In Example 10, 1 g of GB 2 suspended in 10 mL (60 mmol) of the 1.33 HCOOH/NEt$_3$-adduct (AAR=1.33) and 40 mL (286 mmol) of NEt$_3$ were introduced in a rocking stainless-steel autoclave with an internal volume of 120 mL, pressurized with 14.8 g of H$_2$/CO$_2$ 1:1 mixture 98.5 mol-% with 1.5 mol-% CO (316 mmol of H$_2$ and CO$_2$, each, and 9.5 mmol CO) and heated at 40° C. in a water bath. A total pressure of 18.4 MPa abs was attained. Within 160 hours the pressure leveled off to 4.9 MPa abs. The pressure/time curve is shown as curve "C" in FIG. 4. After 160 hours, the autoclave was cooled in ice/water and depressurized. 91 mmol of CO$_2$, 88 mmol of H$_2$ and 10.4 mmol of CO were determined in the vented gases.

In Example 11, Example 10 was repeated but with 1.5 mol-% Ar instead of 1.5 mol-% CO. After 160 hours the pressure leveled off to 4.7 MPa abs. The respective pressure/time curve is shown as curve "B" in FIG. 4. 86 mmol of CO$_2$, 92 mmol of H$_2$, 9.2 mmol of Ar and 0.2 mmol of CO were determined in the vented gases.

Figure 4:
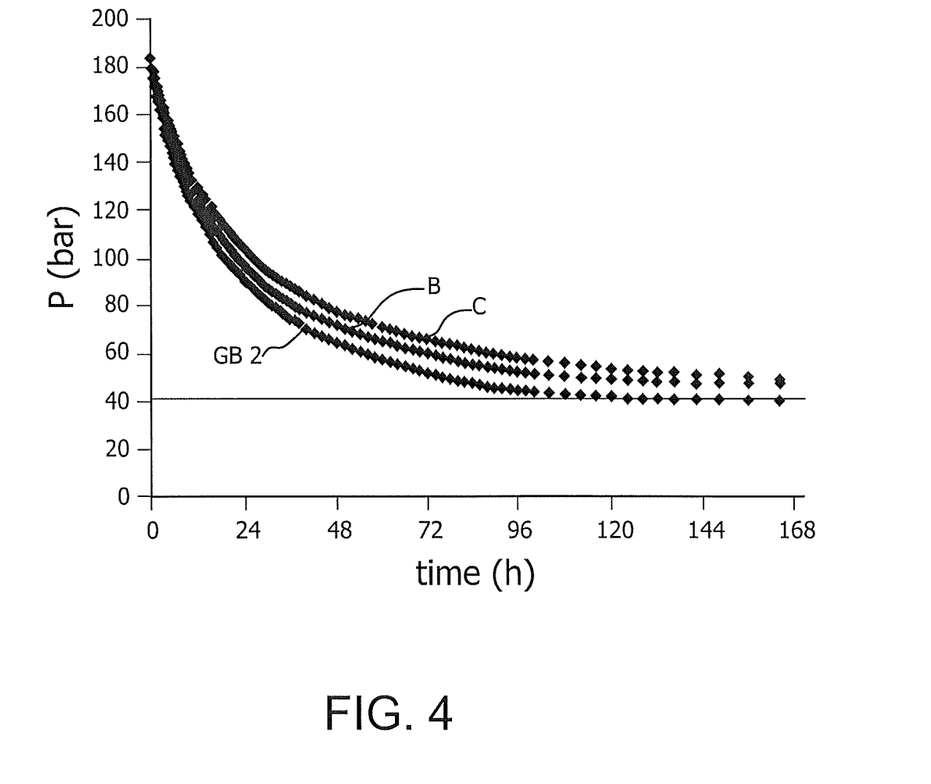
FIG. 4 represents pressure/time curves for Examples 10 and 11. The individual letters have the following meanings: C represents Example 10; B represents Example 11; and GB 2 represents Example 8.

For comparison, curve "GB 2" shows the pressure/time curve of Example 8 (i.e. without addition of CO).

Example 10 shows that even in the presence of 1.5 mol-% CO in the H$_2$/CO$_2$-mixture, a respectable amount of 1.33 HCOOH/NEt$_3$-adduct (AAR=1.33) was produced, which is only 0.3% lower than the amount produced under the same conditions but without the addition of CO.

Example 12

Continuous Production of Adduct (According to the Invention)

Figure 5:
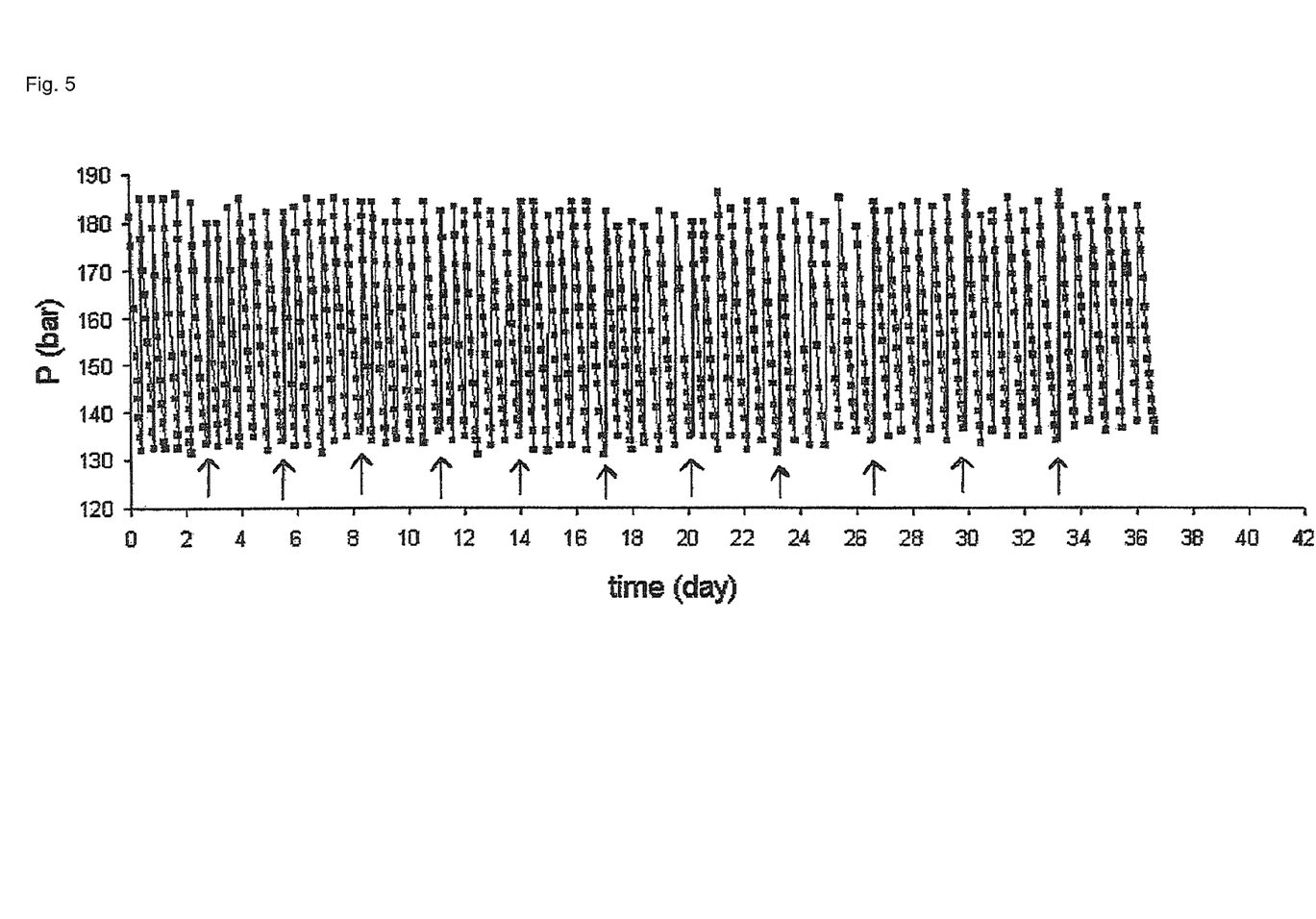
FIG. 5 represents a pressure/time curve based on the continuous production of adduct of Example 12. The arrows represent a short interruption in stirring.

The experimental set-up for example 12 was the same as in example 9, but with the difference that the autoclave additionally contained a steel net ring shaped cage for the fixation of the heterogeneous catalyst. The autoclave was charged with 13 g of AUROlite™ Au/TiO$_2$ and 140 mL (1.0 mol) of NEt$_3$ and pressurized with 46.2 g of H$_2$/CO$_2$ 1:1 mixture (referring to 1004 mmol of H$_2$ and CO$_2$ each). The autoclave was then heated at 40° C. by a heater and a starting pressure of 18.1 MPa abs was attained. As shown in FIG. 5, the pressure slightly decreased with time. Every time the pressure had dropped to about 13 MPa abs, approximately 18 MPa abs (plus/minus a few tenth MPa) were restored by adding further H$_2$/CO$_2$ 1:1 mixture. For this purpose an amount of approximately 8 g of the gas mixture (referring to about 174 mmol of H$_2$ and CO$_2$ each) were required.

At the end of the sixth pressure decrease the stirring was shortly interrupted. In FIG. 5, the interruption is illustrated by an arrow. 100.8 g of clean, colourless, gold free, liquid 1.46 HCOOH/NEt$_3$-adduct (AAR=1.46) were withdrawn from the bottom of the autoclave through the dip tube. The withdrawn amount was depressurized and analyzed. The gas phase contained 8.8 g (200 mmol) of CO$_2$, 70 mg (35 mmol) of H$_2$ and 13.5 mg (0.5 mmol) of CO. H$_2$ and CO were not replaced, while 7.4 g (170 mmol) of CO$_2$ was reintroduced into the autoclave from a reservoir charged with liquid CO$_2$, which was warmed up to 80° C. Then, 83.5 mL (598 mmol) of NEt$_3$ were introduced into the autoclave with the HPLC pump while the stirring was started again. For the next cycle, the autoclave was pressurized again to approximately 18 MPa abs with 15.6 g of H$_2$/CO$_2$ 1:1 mixture (referring to 339 mol of H$_2$ and CO$_2$ each).

In total, twelve of such six-stepped runs were performed within 37 days. The corresponding pressure/time-curves are shown in FIG. 5. After the sixth pressure decrease of the twelfth cycle the procedure was stopped and the autoclave depressurized. The off-gas contained 20.6 g (468 mmol) of CO$_2$, 0.93 g (465 mmol) of H$_2$ and 1.31 g (47 mmol) of CO. A total of 1326 g (7.367 mol) of 1.715 HCOOH/NEt$_3$-adduct (AAR=1.715) was collected during the whole experiment. The total amount of produced CO was 1.76 g (63 mmol).

This experiment shows clearly, that the catalyst will not be poisoned by CO and can be reused several times without a significant loss in activity.

Furthermore, the experiment illustrates that a respectable amount of 1.715 HCOOH/NEt$_3$-adduct (AAR=1.715) was produced over a time of about 37 days. A yield of approx. 93% (7.367 mol×1.715/13.543 mol) bound in the HCOOH/NEt$_3$-adduct with regard to the amounts of introduced H$_2$ and CO$_2$ was attained.

Example 13

Influence of CO to Continuous Production of Adduct (According to the Invention)

Figure 6:
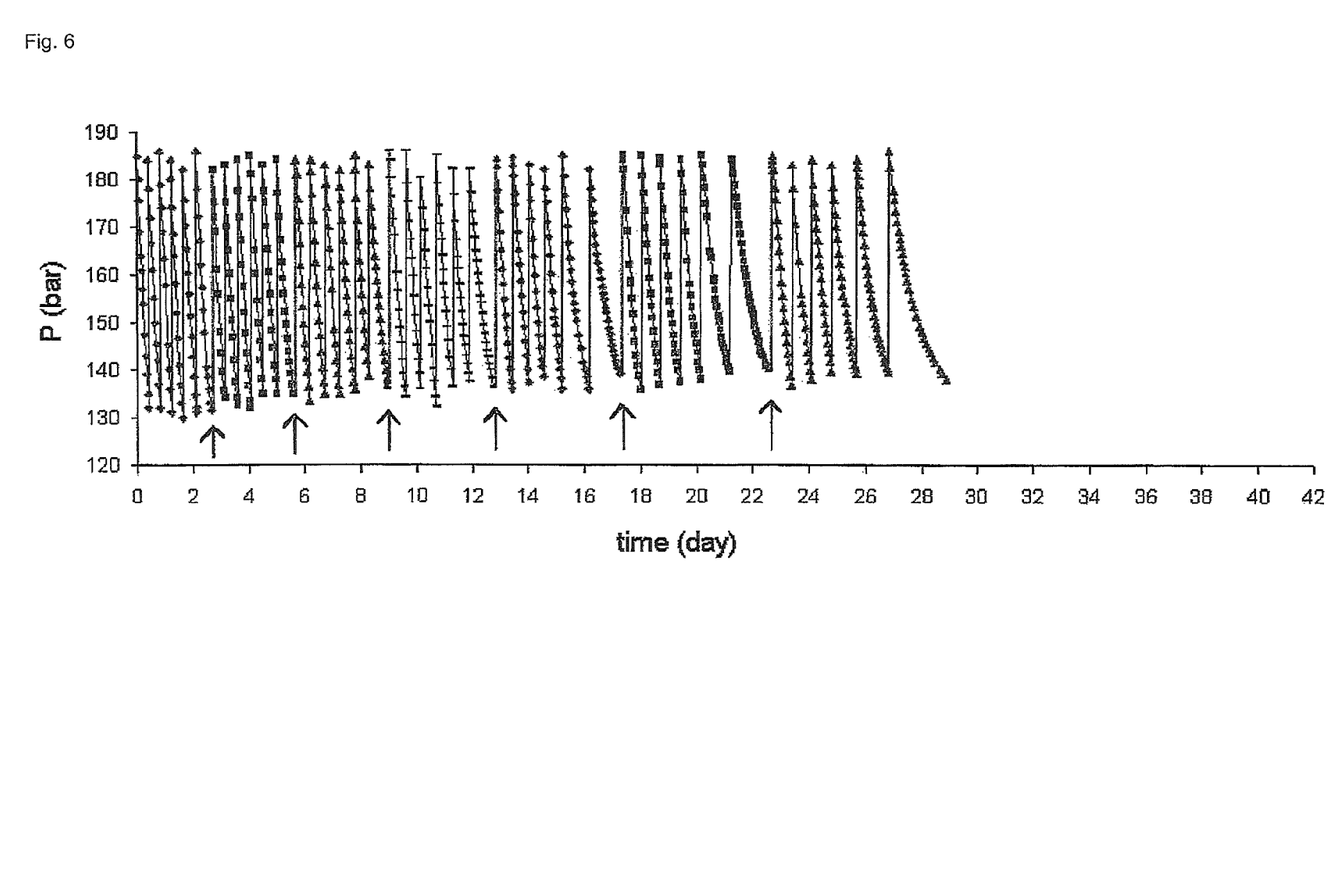
FIG. 6 represents a pressure/time curve based on the continuous production of adduct of Example 13. The arrows represent a short interruption in stirring.

The experimental set-up for example 13 was the same as in example 12, but with the difference that a H$_2$/CO$_2$ 1:1 mixture 99 mol-% with 1.0 mol-% CO was used. For the first cycle, the autoclave containing 13 g of AUROlite™ Au/TiO$_2$ and 140 mL (1.0 mol) of NEt$_3$ was pressurized at 40° C. with 46.2 g of H$_2$/CO$_2$ 1:1 mixture 99 mol-% with 1.0 mol-% CO (referring to 993 mol of H$_2$ and CO$_2$ each and 17.8 mmol of CO). A starting pressure of 18.5 MPa abs was attained, which slightly decreased with time as shown in FIG. 6. Every time the pressure had dropped to about 13 MPa abs, approximately 18 MPa abs (plus/minus a few tenth MPa) were restored by adding further H$_2$/CO$_2$ 1:1 mixture 99 mol-% with 1.0 mol-% CO. For this purpose an amount of approximately 8 g of the gas mixture (referring to about 172 mmol of H$_2$ and CO$_2$ each and 3.5 mmol of CO) were required.

At the end of the sixth pressure decrease the stirring was shortly interrupted. In FIG. 6, the interruption is illustrated by an arrow. 100.6 g of clean, colourless, gold free, liquid 1.46 HCOOH/NEt$_3$-adduct (AAR=1.46) were withdrawn from the bottom of the autoclave through the dip tube. The withdrawn amount was depressurized and analyzed. The gas phase contained 8.6 g (195 mmol) of CO$_2$, 60 mg (30 mmol) of H$_2$ and 51 mg (1.8 mmol) of CO. H$_2$ and CO were not replaced, while 7.3 g (166 mmol) of CO$_2$ was reintroduced into the autoclave from a reservoir charged with liquid CO$_2$, which was warmed up to 80° C. Then, 83.5 mL (598 mmol) of NEt$_3$ were introduced into the autoclave with the HPLC pump while the stirring was started again. For the next cycle, the autoclave was pressurized again to approximately 18 MPa abs with 16 g of H$_2$/CO$_2$ 1:1 mixture 99 mol-% with 1.0 mol-% CO (referring to 344 mol of H$_2$ and CO$_2$ each and 7 mmol of CO).

In total, seven of such six-stepped runs were performed within 29 days. The corresponding pressure/time-curves are shown in FIG. 6. After the sixth pressure decrease of the seventh cycle the procedure was stopped and the autoclave depressurized. The off-gas contained 18.3 g (416 mmol) of 002, 0.83 g (414 mmol) of H$_2$ and 5.4 g (193 mmol) of CO. A total of 790 g (4.455 mol) of 1.657 HCOOH/NEt$_3$-adduct (AAR=1.657) was collected during the whole experiment. The total amount of produced CO was 2.24 g (80 mmol).

Example 13 shows that even in the presence of 1.0 mol-% CO in the H$_2$/CO$_2$-mixture, a respectable amount of 1.657 HCOOH/NEt$_3$-adduct (AAR=1.657) was produced, which is only 2% less formic acid than the amount produced under the same conditions but without the addition of CO. A yield of approx. 91% (4.455 mol×1.657/8.095 mol) bound in the HCOOH/NEt$_3$-adduct with regard to the amounts of introduced H$_2$ and CO$_2$ was attained.

Example 14

Influence of CO to Continuous Production of Adduct (According to the Invention)

Figure 7:
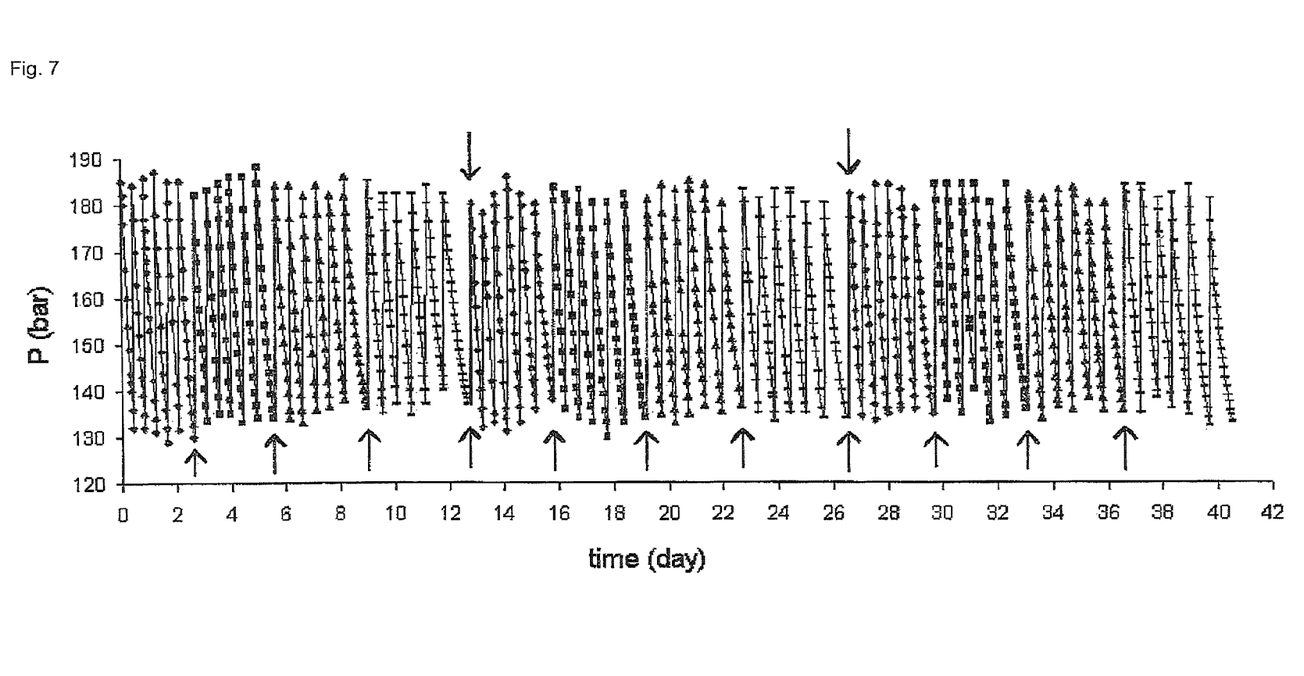
FIG. 7 represents a pressure/time curve based on the continuous production of adduct of Example 14. The arrows below the curve represent a short interruption in stirring. The arrows above the curve represent when the adduct was withdrawn and the gases directly vented from the autoclave.

The experimental set-up for example 14 was the same as in example 13. For the first cycle, the autoclave containing 12.8 g of AUROlite™ Au/TiO$_2$ and 140 mL (1.0 mol) of NEt$_3$ was pressurized at 40° C. with 46 g of H$_2$/CO$_2$ 1:1 mixture 99 mol-% with 1.0 mol-% CO (referring to 989 mol of H$_2$ and CO$_2$ each and 17.2 mmol of CO). A starting pressure of 18.5 MPa abs was attained, which slightly decreased with time as shown in FIG. 7. Every time the pressure had dropped to about 13 MPa abs, approximately 18 MPa abs (plus/minus a few tenth MPa) were restored by adding further H$_2$/CO$_2$ 1:1 mixture 99 mol-% with 1.0 mol-% CO. For this purpose an amount of approximately 8 g of the gas mixture (referring to about 172 mmol of H$_2$ and CO$_2$ each and 3.5 mmol of CO) were required.

At the end of the sixth pressure decrease the stirring was shortly interrupted. In FIG. 7, the interruption is illustrated by an arrow below the pressure/time curve. 100 g of clean, colourless, gold free, liquid 1.47 HCOOH/NEt$_3$-adduct (AAR=1.47) were withdrawn from the bottom of the autoclave through the dip tube. The withdrawn amount was depressurized and analyzed. The gas phase contained 8.4 g (191 mmol) of CO$_2$, 59 mg (29 mmol) of H$_2$ and 50 mg (1.8 mmol) of CO. H$_2$ and CO were not replaced, while 7.1 g (161 mmol) of CO$_2$ was reintroduced into the autoclave from a reservoir charged with liquid CO$_2$, which was warmed up to 80° C. Then, 84 mL (603 mmol) of NEt$_3$ were introduced into the autoclave with the HPLC pump while the stirring was started again. For the next cycle, the autoclave was pressurized again to approximately 18.2 MPa abs with 16.2 g of H$_2$/CO$_2$ 1:1 mixture 99 mol-% with 1.0 mol-% CO (referring to 348 mol of H$_2$ and CO$_2$ each and 6.7 mmol of CO).

Four of such six-stepped runs were performed within 13 days. The corresponding pressure/time-curves are shown in FIG. 7. At the fourth sampling 101.3 g (565 mmol) of 1.7 HCOOH/NEt$_3$-adduct (AAR=1.7) and 22 g (500 mmol) of CO$_2$, 0.90 g (450 mmol) of H$_2$ and 3.0 g (107 mmol) of CO were removed from the autoclave. The adduct was withdrawn and the gases directly vented from the autoclave. This step is indicated in FIG. 7 by a second arrow above the pressure/time curve. Then, 79.5 mL (568 mmol) of NEt$_3$ were introduced into the autoclave with the HPLC pump while the stirring was started again. For the next cycle, the autoclave was pressurized again to approximately 18 MPa abs with 30.6 g of H$_2$/CO$_2$ 1:1 mixture 99 mol-% with 1.0 mol-% CO (referring to 658 mol of H$_2$ and CO$_2$ each and 11 mmol of CO).

Four further six-stepped runs were performed and then another renewal with fresh gas phase as described in the above paragraph accomplished.

After the sixth pressure decrease of the twelfth cycle the procedure was stopped and the autoclave depressurized. The off-gas contained 21.8 g (495 mmol) of CO$_2$, 0.89 g (447 mmol) of H$_2$ and 2.76 g (98 mmol) of CO. A total of 1307 g (7.343 mol) of 1.67 HCOOH/NEt$_3$-adduct (MR=1.67) was collected during the whole experiment. The total amount of produced CO was 2.05 g (73 mmol).

The 1.67 HCOOH/NEt$_3$-adduct (AAR=1.67) was processed in a distillation column at 110° C. and 70 hPa abs, and 297 mL (2.13 mol) of NEt$_3$ distilled off. 1088 g (5.2 mol) of 2.35 HCOOH/NEt$_3$-adduct (AAR=2.35) were obtained as residue.

Also example 14 shows that even in the presence of 1.0 mol-% CO in the H$_2$/CO$_2$-mixture, a respectable amount of 1.67 HCOOH/NEt$_3$-adduct (MR=1.67) was produced, which is only 6% less formic acid than the amount produced under the same conditions but without the addition of CO. A yield of approx. 87% (7.343 mol×1.67/14.083 mol) bound in the HCOOH/NEt$_3$-adduct with regard to the amounts of introduced H$_2$ and CO$_2$ was attained.

Example 15

Base Exchange and Isolation of Formic Acid (According to the Invention)

24 g of 2.35 HCOOH/NEt$_3$-adduct (MR=2.35), which is for example obtainable by distilling off NEt$_3$ from a HCOOH/NEt$_3$-adduct with a lower MR-value at reduced pressure (e.g. at 110° C. and 70 hPa abs), was mixed with 43 g of tri-n-hexylamine (in the following referred to as "NHex$_3$"). On stirring, an opaque liquid was obtained and fractionated under reduced pressure (111 hPa abs) with a short Vigreux column.

When the oil bath temperature had reached 125° C., NEt$_3$ distilled off within the 25-40° C. fraction and 10.5 g (90% of the total amount of NEt$_3$) were collected in a Schlenk tube which was cooled at 0° C., while the residual liquid became limpid. The Schlenk tube was then removed under the reduced pressure mentioned above and the temperature was raised. When the oil bath temperature had reached 160° C., a second fraction begun to distill off and 12.5 g of an acidic liquid were collected. $^1$H NMR showed formic acid with 90% purity (8% NEt$_3$ and 1% NHex$_3$). To obtain formic acid with a higher purity, a further distillation step can be added.

This experiment shows, that it is possible to exchange the low boiling NEt$_3$ (from which formic acid cannot be distilled off) by a high boiling amine like NHex$_3$. From this amine, formic acid can be easily isolated by distillation.

Example 16

Preparation of Formic Acid by Hydrogenation, Base Exchange and Isolation of Formic Acid (According to the Invention)

Figure 8:
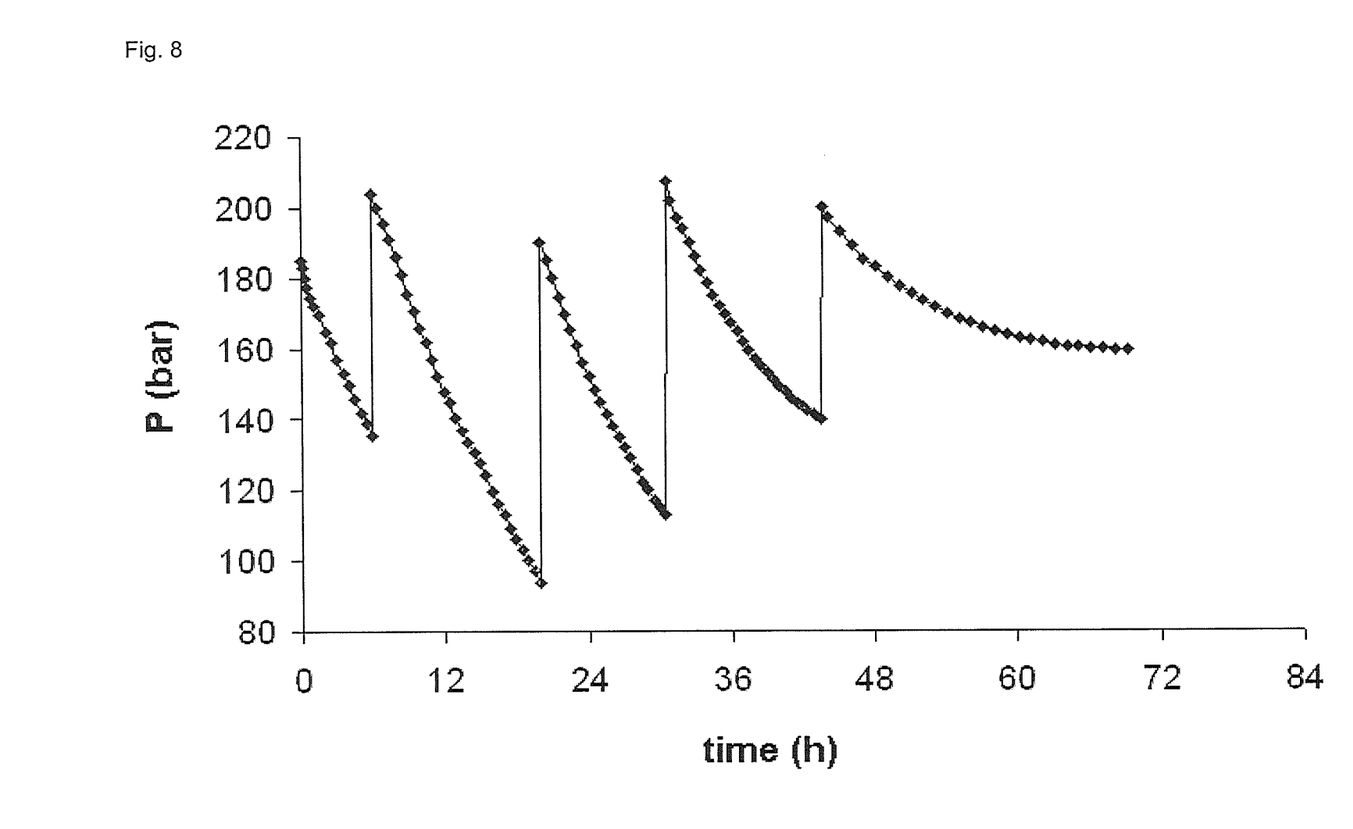
FIG. 8 represents a pressure/time curve for Example 16.

Hydrogenation:
A 120 mL rocking steel autoclave was charged with 21 g (356 mmol) of NMe$_3$, 21.8 g of H$_2$/CO$_2$ 1:1 mixture and 5 g of caged AUROlite™. On stirring at 40° C., the highest detected pressure was 18.5 MPa abs and then decreased as shown in FIG. 8. After having reached approximately 13.5 MPa abs further H$_2$/CO$_2$ 1:1 mixture was added to increase the pressure as shown in FIG. 8. Further pressure de- and increases followed as shown in FIG. 8. At the end, the pressure was left to equilibrate at 16.0 MPa abs. The autoclave was then depressurized and amine-free gases containing 0.8 vol.-% CO vented. 49 mL (50.5 g) of an catalyst-free HCOOH/NMe$_3$ adduct with AAR=1.89 were collected.

Base Exchange:
37 mL of the 1.89 HCOOH/NMe$_3$ adduct (AAR=1.89, referring to 480 mmol of formic acid) from the above hydrogenation step was added to 85.5 mL of NHex$_3$ (245 mmol). Three liquid phases were formed and analyzed by $^1$H NMR. The upper one is constituted by NHex$_3$/NMe$_3$ in a molar ratio of 39:1 with only a trace of formic acid, the intermediate one is constituted by HCOOH/NMe$_3$/NHex$_3$ in a molar ratio of 8.5:1:4.7, and the heaviest one is constituted by HCOOH/NMe$_3$ in a molar ratio of 1.72:1. Then, a stream of a H$_2$/CO$_2$ 1:1 mixture was bubbled through the triphasic system at 130° C. to strip off NMe$_3$. By this, 95% of the NMe$_3$ was recovered together with H$_2$/CO$_2$, having a (H$_2$/CO$_2$)/NMe$_3$ molar ratio of 2, which is a suitable ratio for the new production of HCOOH/NMe$_3$ adducts. During the removal of NMe$_3$ with the H$_2$/CO$_2$ mixture also the traces of water were removed so that a mono-phasic, anhydrous HCOOH/NHex$_3$ adduct with AAR=2 with traces of NMe$_3$ was left.

Isolation of Formic Acid:
The HCOOH/NHex$_3$ adduct (AAR=2) from the above base exchange was then distilled at 160° C. and 133 hPa ab, yielding pure NHex$_3$ and quantitatively anhydrous, raw HCOOH contaminated with 4 vol.-% NHex$_3$ and 1 vol.-% NMe$_3$. The obtained raw HCOOH was finally distilled at 100° C. and atmospheric pressure to give a total yield of formic acid of 92%. The distillation residue contained HCOOH/NMe$_3$/NHex$_3$ in a molar ratio of 6.3:1:1 which can be recycled. This experiments shows, that it is possible to obtain pure formic acid by hydrogenation of CO$_2$ in the presence of a heterogeneous catalyst comprising gold and a low boiling trialkylamine, followed by a base exchange with a high boiling amine and distillation of the formic acid/high boiling amine adduct.

TABLE 1

| Catalyst | | GB 1 | GB 2 |
|---|---|---|---|
| T | [° C.] | 40 | 40 |
| H$_2$ introduced | [mmol] | 304 | 304 |
| CO$_2$ introduced | [mmol] | 304 | 304 |
| NEt$_3$ introduced | [mmol] | 286 | 286 |
| 1.33 adduct introduced | [mmol] | 60 | 60 |
| initial p | [MPa abs] | 18.0 | 18.0 |
| leveled p | [MPa abs] | 10.7 | 4.1 |
| H$_2$ recovered | [mmol] | 196 | 87 |
| CO$_2$ recovered | [mmol] | 196 | 86 |
| free NEt$_3$ | [mmol] | 206 | 122 |
| produced 1.33 adduct | [mmol] | 80 | 163 |

The invention claimed is:

1. A process for preparing formic acid by hydrogenation of carbon dioxide in the presence of a tertiary amine (I) and a catalyst at a pressure of from 0.2 to 30 MPa abs and a temperature of from 0 to 200° C., wherein the catalyst is a heterogeneous catalyst comprising gold.

2. The process according to claim 1, wherein the heterogeneous catalyst comprising gold is a supported catalyst.

3. The process according to claim 2, wherein the supported heterogeneous catalyst comprises silicon dioxide, aluminium oxide, zirconium oxide, magnesium oxide and/or titanium oxide as support.

4. The process according to claim 2, wherein the supported heterogeneous catalyst comprises 0.1 to 20 wt.-% gold based on the total mass of the supported catalyst.

5. The process according to claim 1, wherein the tertiary amine (I) comprises not more than 9 carbon atoms.

6. The process according to claim 1, wherein the tertiary amine (I) is trimethylamine, triethylamine and/or a tripropylamine.

7. The process according to claim 1, wherein the product mixture obtained by the hydrogenation comprising formic acid and tertiary amine (I) is reacted with a tertiary amine (II) which comprises 12 to 48 carbon atoms, the released tertiary amine (I) separated whereby a product mixture comprising formic acid and tertiary amine (II) is obtained, and the formic acid removed from said product mixture by distillation.

8. The process according to claim 7, wherein the tertiary amine (II) is a tripentylamine, a trihexylamine, a triheptylamine, a trioctylamine, methyldicyclohexylamine, a dioctylmethylamine and/or a dimethyldecylamine.

9. The process according to claim 7, wherein the reaction of the product mixture comprising formic acid and tertiary amine (I) with the tertiary amine (II) is performed at temperature of from 20 to 200° C. and a pressure of from 0.01 to 20 MPa abs.

10. The process according to claim 7, wherein the tertiary amine (I), which is released by the reaction of the product mixture comprising formic acid and tertiary amine (I) with tertiary amine (II) and separated, is recycled to the step of the hydrogenation of carbon dioxide.

11. The process according to claim 7, wherein the distillation of the product mixture comprising formic acid and tertiary amine (II) is performed in a distillation apparatus at a bottom temperature of from 100 to 300° C. and a pressure of from 30 to 3000 hPa abs.

12. The process according to claim 7, wherein in the step of the removal of formic acid by distillation a bottom product containing tertiary amine (II) is obtained and recycled to the step of the reaction of the product mixture comprising formic acid and tertiary amine (I) with tertiary amine (II).

* * * * *